US012678065B2

(12) United States Patent
Hsieh et al.

(10) Patent No.: US 12,678,065 B2
(45) Date of Patent: Jul. 14, 2026

(54) ELECTRONIC DEVICE, CAPILLARY REFILL TIME DETERMINING SYSTEM AND CAPILLARY REFILL TIME DETERMINING METHOD

(71) Applicant: China Medical University, Taichung City (TW)

(72) Inventors: Kai-Sheng Hsieh, Kaohsiung City (TW); Chun-Yen Lin, Taipei City (TW); Bo-Yen Chang, Taipei City (TW); Yen-Chieh Wang, New Taipei City (TW)

(73) Assignee: China Medical University, Taichung City (TW)

( * ) Notice: Subject to any disclaimer, the term of this patent is extended or adjusted under 35 U.S.C. 154(b) by 0 days.

(21) Appl. No.: 18/636,654

(22) Filed: Apr. 16, 2024

(65) Prior Publication Data

US 2024/0341611 A1      Oct. 17, 2024

(30) Foreign Application Priority Data

Apr. 17, 2023      (TW) .................................. 112114245

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/0077* (2013.01); *A61B 5/1032* (2013.01);
(Continued)

(58) Field of Classification Search
CPC ..... A61B 5/022; A61B 5/1032; A61B 5/0261; A61B 5/0077; A61B 5/6898; A61B 5/742; G16H 50/70
See application file for complete search history.

(56) References Cited

U.S. PATENT DOCUMENTS 8,899,748 B1 * 12/2014 Migdal .................. A61B 5/004
                                                                    351/210
2017/0238842 A1 * 8/2017 Jacquel .................. A61B 5/746
(Continued)

FOREIGN PATENT DOCUMENTS

TW            201038256 A      11/2010

*Primary Examiner* — John D Li
(74) *Attorney, Agent, or Firm* — SERVILLA WHITNEY LLC

(57) ABSTRACT

A capillary refill time determining system is configured to judge a color variation of an image, and the capillary refill time determining system includes an electronic device including an image capturing unit, a storage unit and a processor. The storage unit is configured to access a refill start time and a default value. The processor is electronically connected to the image capturing unit and the storage unit, and the processor is configured to analyze an average color value of the image at an initial period, wherein at least one refill color value is obtained by analyzing the image according to the refill start time, the difference between the average color value and the refill color value is confirmed whether less than or equal to the default value, and a refill period is calculated between the refill start time and the refill end time.

15 Claims, 8 Drawing Sheets

S200

S201 —~ initial period image analysis step

S202 —~ refill period image analysis step

S203 —~ comparison step

(51) Int. Cl.
  _A61B 5/103_ (2006.01)
  _G16H 50/70_ (2018.01)

(52) U.S. Cl.
  CPC ............ _A61B 5/6898_ (2013.01); _A61B 5/742_
  (2013.01); _G16H 50/70_ (2018.01)

(56) References Cited

U.S. PATENT DOCUMENTS

| | | | |
|---|---|---|---|
| 2018/0128714 A1* | 5/2018 | Adey ........................ | G01N 1/06 |
| 2018/0271382 A1* | 9/2018 | Bezemer .............. | A61B 5/0013 |
| 2019/0223763 A1* | 7/2019 | Schwartz ............... | G16H 40/63 |
| 2020/0352437 A1* | 11/2020 | Yang ................... | A61B 5/7214 |
| 2023/0083633 A1* | 3/2023 | Desai ................... | G16H 10/60 |
| | | | 726/19 |

* cited by examiner

100

110

111 image
capturing unit display unit

112

113 storage unit

114 processor

S200

ELECTRONIC DEVICE, CAPILLARY REFILL TIME DETERMINING SYSTEM AND CAPILLARY REFILL TIME DETERMINING METHOD

RELATED APPLICATIONS

This application claims priority to Taiwan Application Serial Number 112114245, filed Apr. 17, 2023, which is herein incorporated by reference.

BACKGROUND

Technical Field

The present disclosure relates to an electronic device, a capillary refill time determining system and a capillary refill time determining method. More particularly, the present disclosure relates to an electronic device, a capillary refill time determining system and a capillary refill time determining method applicable to mobile devices.

Description of Related Art

In clinically, a diagnostician mainly judges whether a subject has a problem of abnormal peripheral blood circulation by judging the capillary refill time whether exceeding 2 seconds or not. However, how to judge the capillary refill time whether exceeding 2 seconds is difficult to objectively determine based on the medical science, and the problems, such as influencing via the external factors and the excessively subjective judgment of the data via the naked eyes, may be caused, so that the misjudgment of the capillary refill time is easily caused under the emergency condition. Therefore, the requirements of an electronic device, a capillary refill time determining system and a capillary refill time determining method, which can objectively and instantly judge the capillary refill time, need to be developed.

SUMMARY

According to one aspect of the present disclosure, a capillary refill time determining system is configured to judge a color variation of an image, and the capillary refill time determining system includes an electronic device. The electronic device includes an image capturing unit, a storage unit and a processor. The image capturing unit is configured to capture the image. The storage unit is configured to access a refill start time and a default value. The processor is electronically connected to the image capturing unit and the storage unit, the processor receives the image and the refill start time, and the processor is configured to analyze an average color value of the image at an initial period, wherein at least one refill color value is obtained by analyzing the image according to the refill start time, a difference between the average color value and the refill color value is calculated, the difference is confirmed whether less than or equal to the default value to form a color judgment result, a refill end time is currently recorded according to the color judgment result, and a refill period is calculated between the refill start time and the refill end time. The initial period occurs before the refill start time.

According to one aspect of the present disclosure, an electronic device includes an image capturing unit, a display unit, a storage unit and a processor. The image capturing unit is configured to capture an image. The display unit has a sensing area, the display unit displays a background color at the sensing area, and the background color is blue or green. The storage unit is configured to access a refill start time and a default value. The processor is electronically connected to the image capturing unit and the storage unit, the processor receives the image and the refill start time, and the processor is configured to analyze an average color value of the image at an initial period, wherein at least one refill color value is obtained by analyzing the image according to the refill start time, a difference between the average color value and the refill color value is calculated, the difference is confirmed whether less than or equal to the default value to form a color judgment result, a refill end time is currently recorded according to the color judgment result, and a refill period is calculated between the refill start time and the refill end time. The initial period occurs before the refill start time.

According to one aspect of the present disclosure, a capillary refill time determining method is configured to judge a color variation of an image, and the capillary refill time determining method includes an initial period image analysis step and a refill period image analysis step. The initial period image analysis step includes analyzing an average color value of the image at an initial period via a processor. The refill period image analysis step includes analyzing the image for obtaining at least one refill color value according to a refill start time via the processor, calculating a difference between the average color value and the refill color value, confirming the difference whether less than or equal to a default value to form a color judgment result, currently recording a refill end time according to the color judgment result, and calculating a refill period between the refill start time and the refill end time. The initial period occurs before the refill start time.

DETAILED DESCRIPTION

Figure 1:
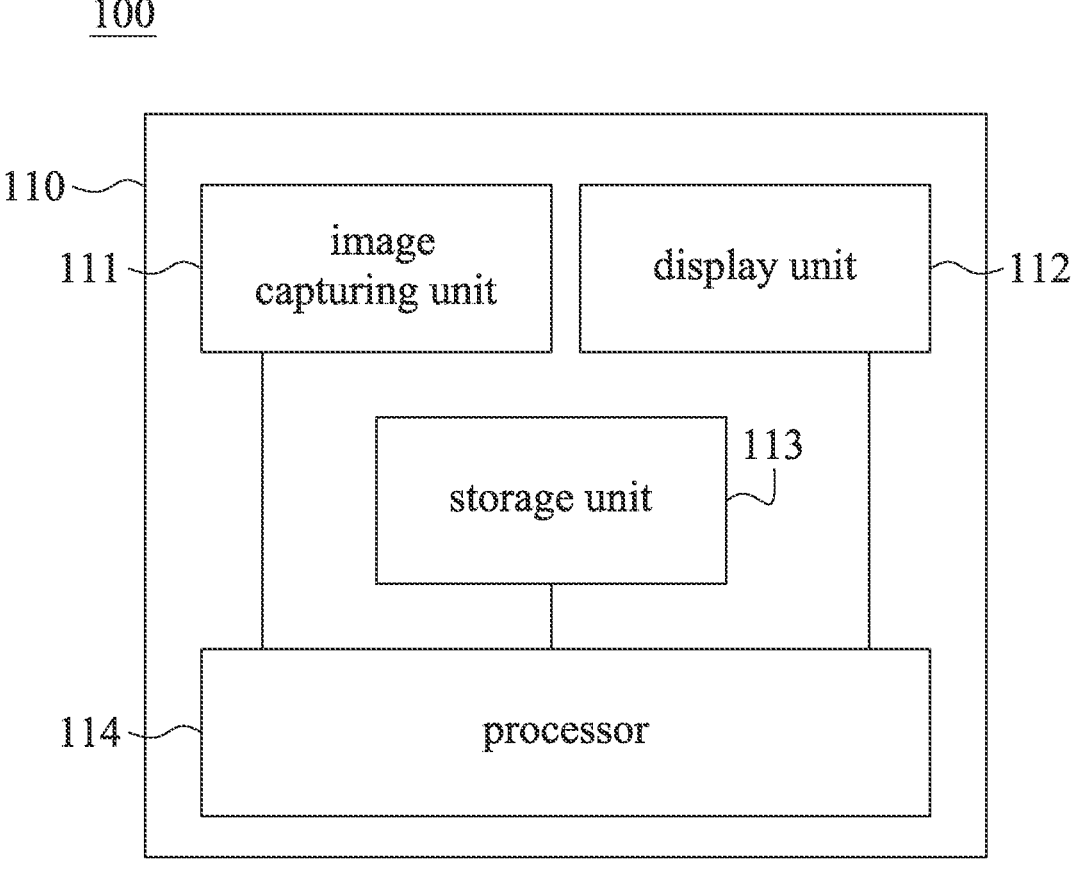
FIG. 1 is a block diagram of a capillary refill time determining system according to the 1st example of the present disclosure.
Figure 2:
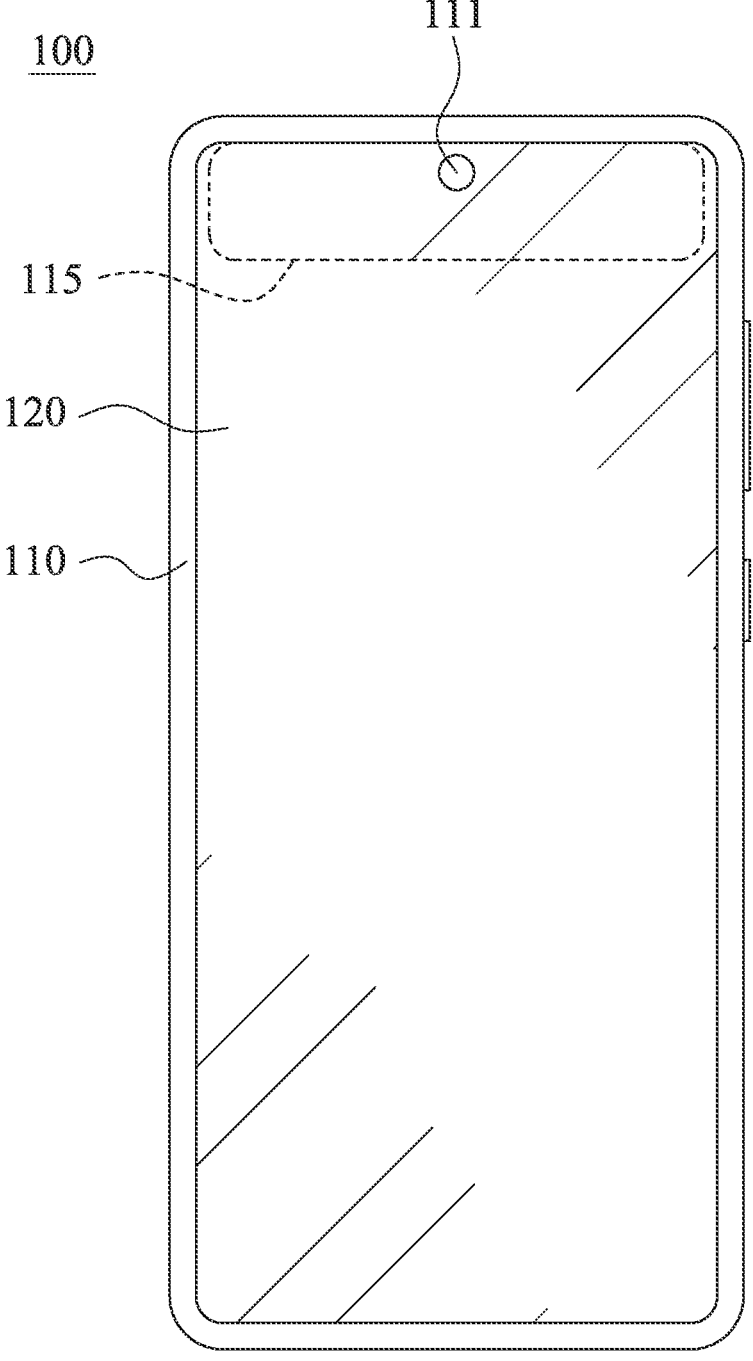
FIG. 2 is a schematic view of the capillary refill time determining system according to the 1st example in FIG. 1.

FIG. 1 is a block diagram of a capillary refill time determining system 100 according to the 1st example of the present disclosure. FIG. 2 is a schematic view of the capillary refill time determining system 100 according to the 1st example in FIG. 1. In FIGS. 1 and 2, the capillary refill time determining system 100 is configured to judge a color variation of an image, and the capillary refill time determining system 100 includes an electronic device 110, wherein the electronic device 110 includes an image capturing unit 111, a display unit 112, a storage unit 113 and a processor 114.

The image capturing unit 111 is configured to capture the image of a tested subject F (labelled in FIG. 4), and the tested subject F entirely covers the image capturing unit 111, wherein the image capturing unit 111 can be a front lens of a mobile phone or a fingerprint identifier, and the tested subject F can be a finger of a subject. Hence, the step of removing a background of the tested subject F can be saved and environmental factors of color difference can be eliminated by entirely covering the image capturing unit 111 via the tested subject F. Further, an allowed calibrating range of the image capturing unit 111 of the front lens of the mobile phone is less, and hence the image can be more accurately captured so as to avoid the color calibration error owing to the equipment.

The display unit 112 has a sensing area 115, the display unit 112 displays a background color at the sensing area 115, and the background color is blue or green, wherein the display unit 112 can be a mobile screen for providing a light, and the display unit 112 can display a dynamic light to adjust the background color. Hence, the color variation of the capillary can be more sensitively determined via the blue background or the green background. In particular, the color variation of the tested subject F is from red to white, and hence the blue light or the green light easily penetrates a surface layer of the tested subject F so as to enhance the judgment of the color variation of the tested subject F.

The storage unit 113 is configured to access a refill start time Ts (labelled in FIG. 8) and a default value.

The processor 114 is electronically connected to the image capturing unit 111, the display unit 112 and the storage unit 113, the processor 114 receives the image and the refill start time Ts, and the processor 114 is configured to analyze an average color value of the image at an initial period T1 (labelled in FIG. 8), wherein at least one refill color value is obtained by analyzing the image according to the refill start time Ts, a difference between the average color value and the refill color value is calculated, the difference is confirmed whether less than or equal to the default value to form a color judgment result, a refill end time Te (labelled in FIG. 8) is currently recorded according to the color judgment result, and a refill period T3 (labelled in FIG. 8) is calculated between the refill start time Ts and the refill end time Te. The initial period T1 occurs before the refill start time Ts. Moreover, the image is processed via the processor 114 with a software structure python 3, and the image, the average color value, the refill color value, the difference, the color judgment result, the refill end time Te and the refill period T3 can be uploaded to a cloud via the internet of things (IoT).

When the color judgment result is yes (that is, the difference between the average color value and the refill color value is less than or equal to the default value), the refill end time Te is currently recorded, and the refill period T3 is calculated between the refill start time Ts and the refill end time Te. It should be mentioned that the color value is a value of RGB, an R value is mainly captured while judging the color variation of the tested subject F, and the default value is a predetermined certain level of the color value of the image at the refill start time Ts (that is the tested subject F under pressure) recovering to the color value of the image at the initial period T1 (that is the tested subject F not yet under pressure). For example, the color value of the image at the refill start time Ts is recovered at least ninety percent of the color value of the image at the initial period T1, but the present disclosure is not limited thereto.

Furthermore, when the difference between the average color value and the refill color value is larger than the default value over a predetermined time, the processor 114 can be forced to stop. In detail, when the color judgment result continues to fail to be yes (that is, the difference between the average color value and the refill color value continues to be larger than the default value), the user can set the predetermined time for forcing the process of the processor 114 to stop, and the tested result of the tested subject F is directly judged as abnormal, wherein the predetermined time can be 5 seconds, but the present disclosure is not limited thereto.

The storage unit 113 can be configured to access an average refill time for normal people, and the processor 114 is configured to compare the refill period T3 with the average refill time for the normal people, wherein the average refill time for the normal people is less than or equal to 2 seconds, but the present disclosure is not limited thereto. Therefore, the peripheral circulation condition of the tested subject F can be auxiliary evaluated.

The processor 114 is configured to segment the image at an interval, and the interval can be less than or equal to 0.02 seconds, wherein the image can be segmented into pictures via the processor 114 with an image processing software opencv, and the interval can be 0.016 seconds (that is 60 frames), but the present disclosure is not limited thereto.

The processor 114 can be configured to execute an application program APP (labelled in FIG. 4) for prompting a measuring process and controlling the display unit 112. Therefore, the subject can clearly know the current actions under the requirement.

The capillary refill time determining system 100 can further include a protective membrane 120 at least disposed on a surface of the image capturing unit 111 of the electronic device 110. In particular, the protective membrane 120 can be a protective membrane of a mobile screen or an isolation film, and the protective membrane 120 can be configured to prevent the tested subject F from polluting a surface of the image capturing unit 111. Moreover, the protective membrane 120 is transparent so as to avoid influencing the judgment of the capillary refill time determining system 100.

Figure 3:
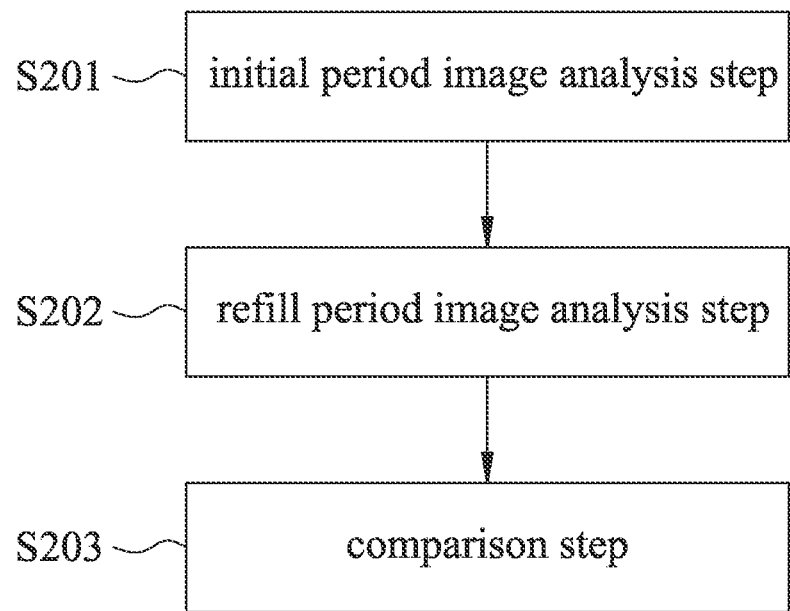
FIG. 3 is a flow chart of a capillary refill time determining method according to the 2nd example of the present disclosure.
Figure 4:
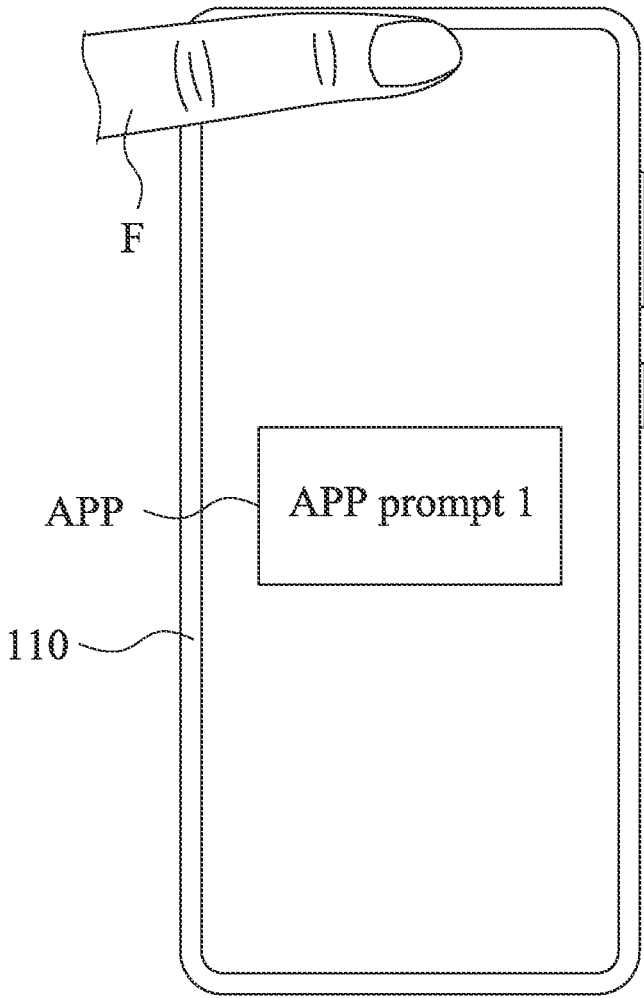
FIG. 4 is a schematic view of an initial period image analysis step according to the 2nd example in FIG. 3.
Figure 5:
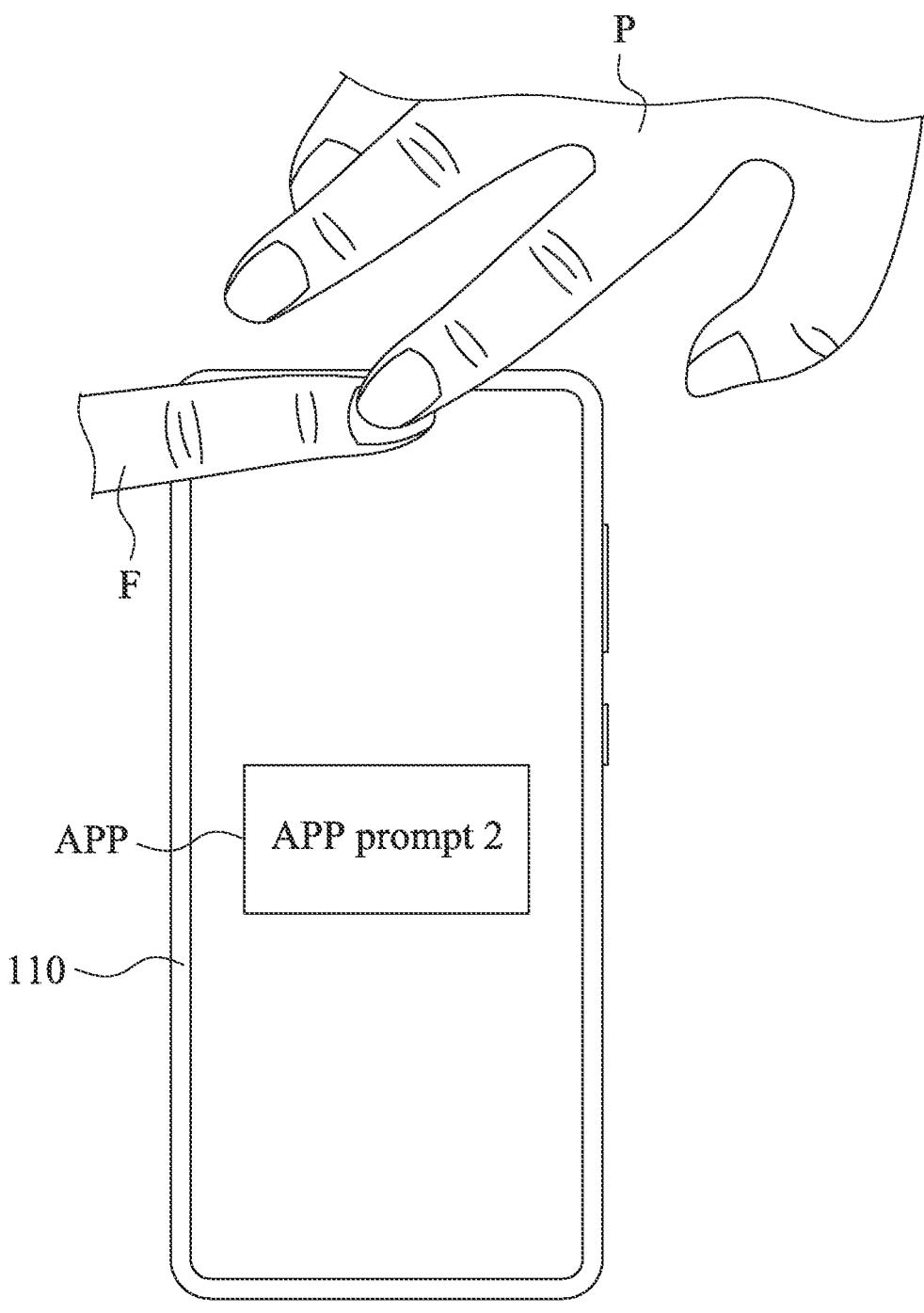
FIG. 5 is a schematic view of pressing the tested subject according to the 2nd example in FIG. 3.
Figure 6:
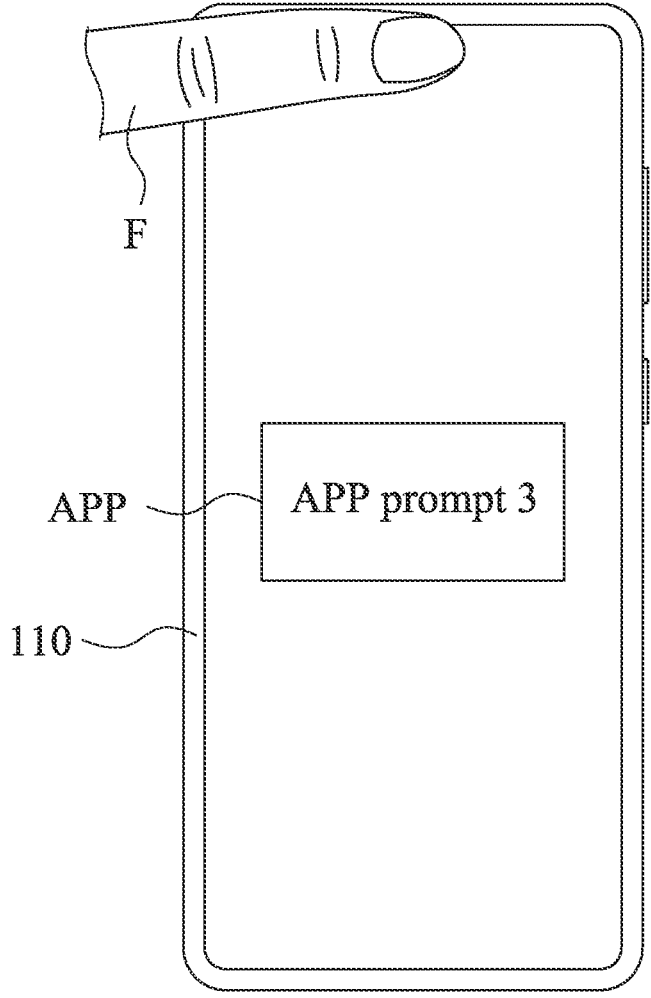
FIG. 6 is a schematic view of stop pressing the tested subject according to the 2nd example in FIG. 3.
Figure 7:
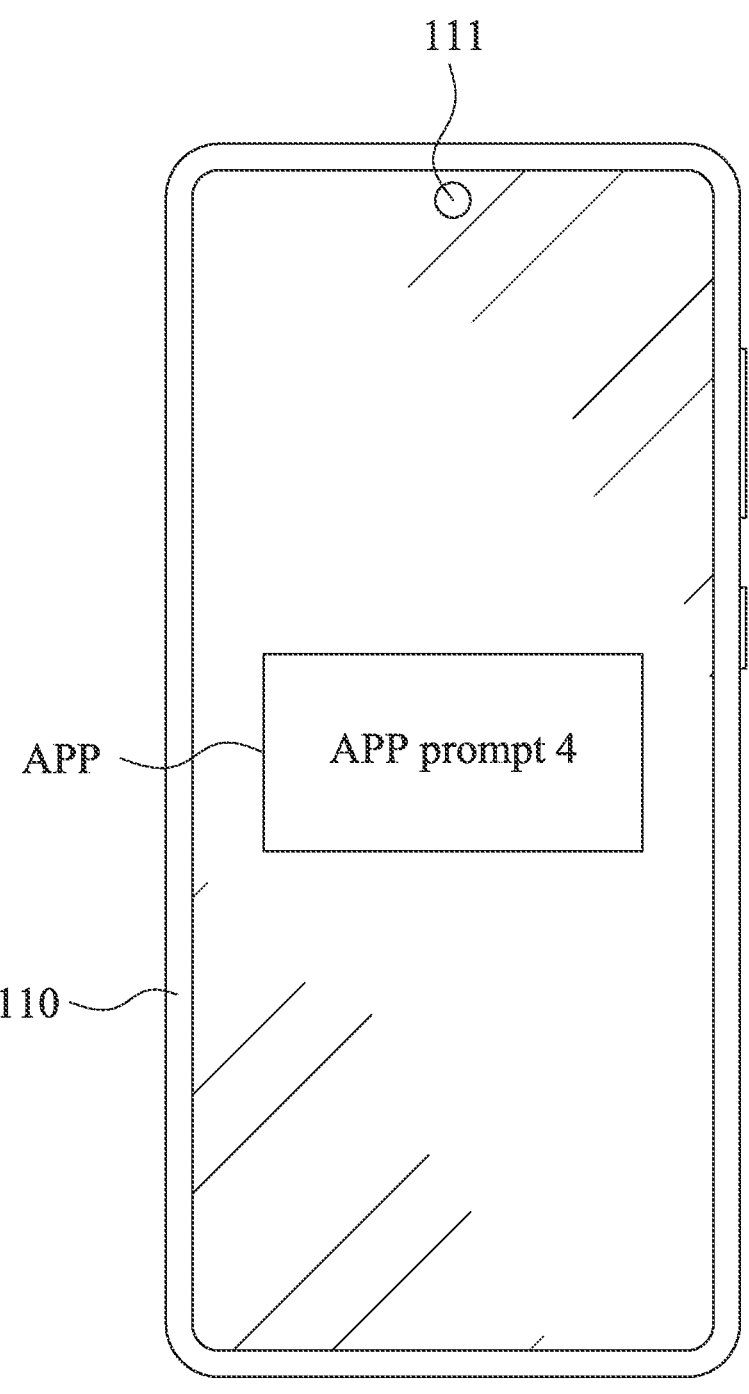
FIG. 7 is a schematic view of a refill period image analysis step according to the 2nd example in FIG. 3.
Figure 8:
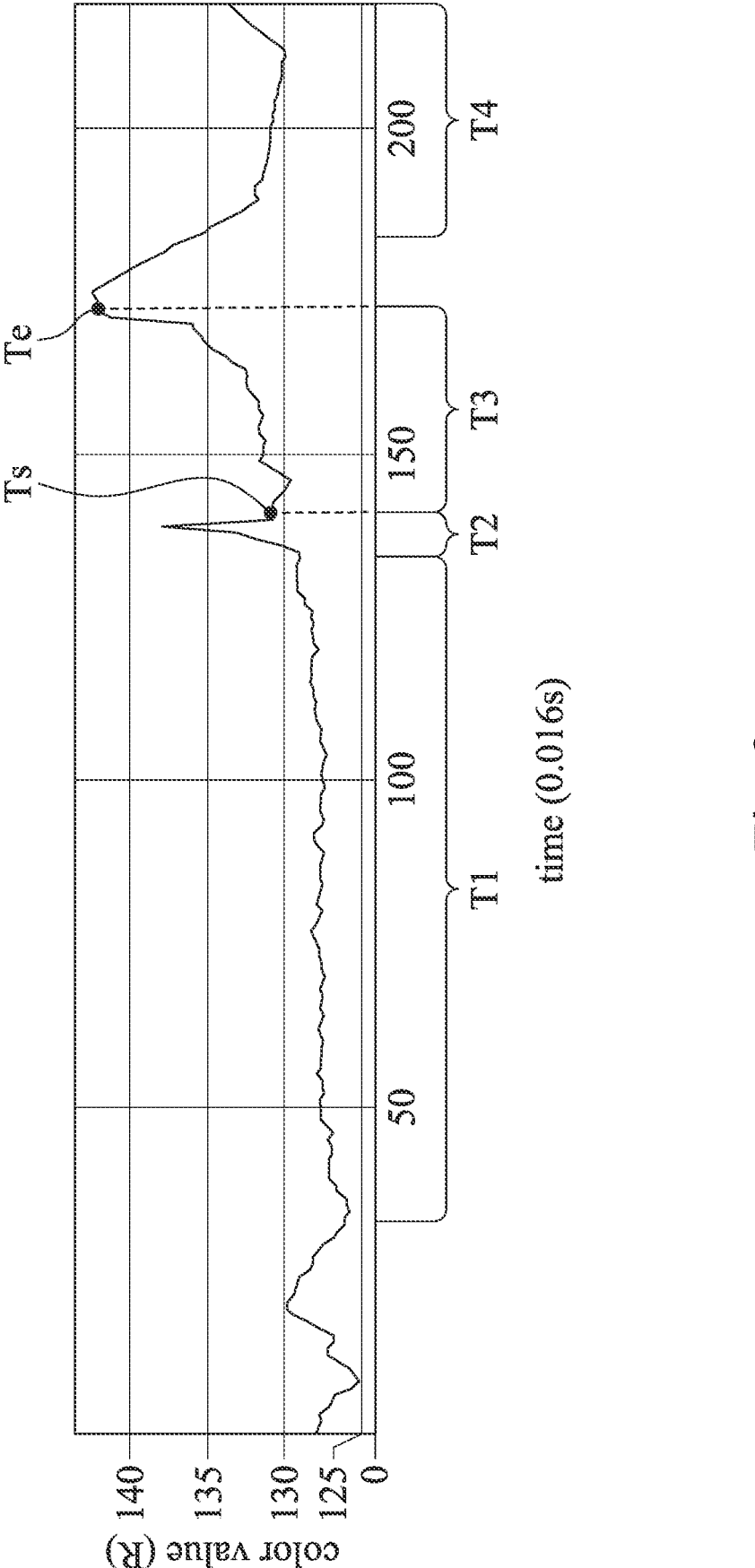
FIG. 8 is a continuous record chart of the capillary refill time according to the 2nd example in FIG. 3.

FIG. 3 is a flow chart of a capillary refill time determining method S200 according to the 2nd example of the present disclosure. FIG. 4 is a schematic view of an initial period image analysis step S201 according to the 2nd example in FIG. 3. FIG. 5 is a schematic view of pressing the tested subject F according to the 2nd example in FIG. 3. FIG. 6 is a schematic view of stop pressing the tested subject F according to the 2nd example in FIG. 3. FIG. 7 is a schematic view of a refill period image analysis step S202 according to the 2nd example in FIG. 3. FIG. 8 is a continuous record chart of the capillary refill time according to the 2nd example in FIG. 3. In FIGS. 3 to 8, the capillary refill time determining method S200 is configured to judge the color variation of the image, and the capillary refill time determining method S200 includes the following steps: the initial period image analysis step S201, the refill period image analysis step S202 and a comparison step S203, wherein the display unit 112 is configured to display the background color of the sensing area 115 from the initial period T1 to the refill end time Te, and the background color is blue or green. In detail, the capillary refill time determining method S200 can be cooperated with the capillary refill time determining system 100 according to the 1st example, and hence the following reference numerals of the elements are referred to FIGS. 1 and 2.

In FIGS. 3, 4 and 8, the initial period image analysis step S201 includes analyzing an average color value of the image at the initial period T1 via the processor 114, wherein the application program APP is configured to prompt the subject to cover the image capturing unit 111 with the tested subject F, and the color value of the image at the initial period T1 is between 125 and 130.

In FIGS. 3, 5 and 8, the application program APP is configured to prompt the subject to stress the tested subject F with a pressurizing object P at a pressurizing period T2, wherein the pressurizing object P can be a finger of a helper, and the color value of the image at the pressurizing period T2 is between 130 and 140.

In FIGS. 3 and 6-8, the refill period image analysis step S202 includes analyzing the image for obtaining at least one refill color value according to the refill start time Ts via the processor 114, calculating a difference between the average color value and the refill color value, confirming the difference whether less than or equal to the default value to form the color judgment result, currently recording the refill end time Te according to the color judgment result, and calculating the refill period T3 between the refill start time Ts and the refill end time Te. In particular, the application program APP is configured to prompt the pressurizing object P to stop pressing the tested subject F, the refill period T3 of the image begins to be calculated via the processor 114, and the application program APP is configured to display the refill period T3 and prompt the tested subject F to leave the image capturing unit 111 after finishing the calculating the refill period T3 of the image, wherein the beginning of the refill start time Ts is when the application program APP is configured to prompt to stop pressurization, but the present disclosure is not limited thereto. Furthermore, when the application program APP is configured to prompt the tested subject F to leave the image capturing unit 111, such as a tested subject leaving period T4, the background color of the sensing area 115 recovers to the normal screen color.

Moreover, the comparison step S203 includes comparing the refill period T3 with the average refill time for the normal people of a comparison database of the processor 114 via the processor 114. Therefore, the peripheral circulation condition of the tested subject F can be auxiliary evaluated.

In summary, by the electronic device, the capillary refill time determining system and the capillary refill time determining method of the present disclosure, the problem of subjectively judging the capillary refill time can be solved so as to prevent from the problem of the inaccurate judgment result, and the condition that the external factors influencing the judging result can be avoided, wherein the external factors can be age, body temperature and skin color. Further, the electronic device, the capillary refill time determining system and the capillary refill time determining method of the present disclosure can be applied to the objective physiological testing of patients under the home care, so that the physiological judging references of the patients can be instantly and objectively provided to the relevant medical staffs for judging.

The foregoing description, for purpose of explanation, has been described with reference to specific examples. It is to be noted that Tables show different data of the different examples; however, the data of the different examples are obtained from experiments. The examples were chosen and described in order to best explain the principles of the disclosure and its practical applications, to thereby enable others skilled in the art to best utilize the disclosure and various examples with various modifications as are suited to the particular use contemplated. The examples depicted above and the appended drawings are exemplary and are not intended to be exhaustive or to limit the scope of the present disclosure to the precise forms disclosed. Many modifications and variations are possible in view of the above teachings.

What is claimed is:

1. A capillary refill time determining system, configured to judge a color variation of an image, and the capillary refill time determining system comprising:

an electronic device, comprising:

an image capturing unit configured to capture the image;

a storage unit configured to access a refill start time and a default value; and a processor electronically connected to the image capturing unit and the storage unit, the processor receiving the image and the refill start time, and the processor configured to analyze an average color value of the image at an initial period, wherein at least one refill color value is obtained by analyzing the image according to the refill start time, a difference between the average color value and the at least one refill color value is calculated, the difference is confirmed whether less than or equal to the default value to form a color judgment result, a refill end time is currently recorded according to the color judgment result, and a refill period is calculated between the refill start time and the refill end time;

wherein the initial period occurs before the refill start time;

wherein the capillary refill time determining system further comprises:

a protective membrane at least disposed on a surface of the image capturing unit of the electronic device;

wherein the electronic device further comprises:

a display unit having a sensing area, the display unit displaying a background color at the sensing area, and the background color being blue;

wherein when the difference between the average color value and the at least one refill color value is larger than the default value over a predetermined time, the processor is forced to stop;

wherein the predetermined time is 5 seconds and larger than an average refill time for normal people.

2. The capillary refill time determining system of claim 1, wherein the display unit displays a dynamic light to adjust the background color.

3. The capillary refill time determining system of claim 1, wherein the processor is configured to execute an application program for prompting a measuring process and controlling the display unit.

4. The capillary refill time determining system of claim 1, wherein when the difference between the average color value and the at least one refill color value is less than or equal to the default value, the refill end time is currently recorded, and the refill period is calculated between the refill start time and the refill end time.

5. The capillary refill time determining system of claim 1, wherein the storage unit is configured to access the average refill time for normal people, and the processor is configured to compare the refill period with the average refill time for the normal people.

6. The capillary refill time determining system of claim 1, wherein the processor is configured to segment the image at an interval, and the interval is less than or equal to 0.02 seconds.

7. An electronic device, comprising:

an image capturing unit configured to capture an image;

a display unit having a sensing area, the display unit displaying a background color at the sensing area, and the background color being blue;

a storage unit configured to access a refill start time and a default value; and a processor electronically connected to the image capturing unit and the storage unit, the processor receiving the image and the refill start time, and the processor configured to analyze an average color value of the image at an initial period, wherein at least one refill color value is obtained by analyzing the image according to the refill start time, a difference between the average color value and the at least one refill color value is calculated, the difference is confirmed whether less than or equal to the default value to form a color judgment result, a refill end time is currently recorded according to the color judgment result, and a refill period is calculated between the refill start time and the refill end time;

wherein the initial period occurs before the refill start time;

wherein a protective membrane at least disposed on a surface of the image capturing unit;

wherein when the difference between the average color value and the at least one refill color value is larger than the default value over a predetermined time, the processor is forced to stop;

wherein the predetermined time is 5 seconds and larger than an average refill time for normal people.

8. The electronic device of claim 7, wherein when the difference between the average color value and the at least one refill color value is less than or equal to the default value, the refill end time is currently recorded, and the refill period is calculated between the refill start time and the refill end time.

9. The electronic device of claim 7, wherein the display unit displays a dynamic light to adjust the background color.

10. The electronic device of claim 7, wherein the storage unit is configured to access the average refill time for normal people, and the processor is configured to compare the refill period with the average refill time for the normal people.

11. The electronic device of claim 7, wherein the processor is configured to execute an application program for prompting a measuring process and controlling the display unit.

12. The electronic device of claim 7, wherein the processor is configured to segment the image at an interval, and the interval is less than or equal to 0.02 seconds.

13. A capillary refill time determining method, configured to judge a color variation of an image, and the capillary refill time determining method comprising:

an initial period image analysis step, comprising analyzing an average color value of the image at an initial period via a processor; and a refill period image analysis step, comprising analyzing the image for obtaining at least one refill color value according to a refill start time via the processor, calculating a difference between the average color value and the at least one refill color value, confirming the difference whether less than or equal to a default value to form a color judgment result, currently recording a refill end time according to the color judgment result, and calculating a refill period between the refill start time and the refill end time;

wherein the initial period occurs before the refill start time;

wherein the capillary refill time determining method is cooperated with a capillary refill time determining system, and the capillary refill time determining system comprises an electronic device and a protective membrane at least disposed on a surface of an image capturing unit of the electronic device;

wherein the electronic device comprises:

a display unit having a sensing area, the display unit displaying a background color at the sensing area, and the background color being blue;

wherein when the difference between the average color value and the at least one refill color value is larger than the default value over a predetermined time, the processor is forced to stop;

wherein the predetermined time is 5 seconds and larger than an average refill time for normal people.

14. The capillary refill time determining method of claim 13, further comprising:

a comparison step, comprising comparing the refill period with the average refill time for normal people of a comparison database of the processor via the processor.

15. The capillary refill time determining method of claim 13, wherein when the difference between the average color value and the at least one refill color value is less than or equal to the default value, the refill end time is currently recorded, and the refill period is calculated between the refill start time and the refill end time.

* * * * *